(12) United States Patent
Sabelle

(10) Patent No.: US 9,233,057 B2
(45) Date of Patent: Jan. 12, 2016

(54) PARTICULAR QUINONE DIRECT DYES, DYE COMPOSITION COMPRISING AT LEAST ONE SUCH DYE, IMPLEMENTATION PROCESS THEREFOR AND USE THEREOF

(71) Applicant: L'OREAL, Paris (FR)

(72) Inventor: Stephane Sabelle, Paris (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/365,224

(22) PCT Filed: Dec. 13, 2012

(86) PCT No.: PCT/EP2012/075386
§ 371 (c)(1),
(2) Date: Jun. 13, 2014

(87) PCT Pub. No.: WO2013/087770
PCT Pub. Date: Jun. 20, 2013

(65) Prior Publication Data
US 2014/0360523 A1 Dec. 11, 2014

Related U.S. Application Data

(60) Provisional application No. 61/584,996, filed on Jan. 10, 2012.

(30) Foreign Application Priority Data

Dec. 13, 2011 (FR) ..................................... 11 61575

(51) Int. Cl.
| | |
|---|---|
| *A61Q 5/10* | (2006.01) |
| *A61K 8/35* | (2006.01) |
| *A61K 8/41* | (2006.01) |
| *C07C 215/82* | (2006.01) |
| *C07C 225/28* | (2006.01) |
| *C07C 251/82* | (2006.01) |
| *A61Q 5/06* | (2006.01) |
| *C09B 23/01* | (2006.01) |

(52) U.S. Cl.
CPC . *A61K 8/355* (2013.01); *A61K 8/41* (2013.01); *A61K 8/411* (2013.01); *A61K 8/415* (2013.01); *A61Q 5/065* (2013.01); *A61Q 5/10* (2013.01); *C07C 215/82* (2013.01); *C07C 225/28* (2013.01); *C07C 251/82* (2013.01); *C09B 23/0066* (2013.01); *A61K 2800/10* (2013.01)

(58) Field of Classification Search
CPC ....... A61Q 5/10; C09B 23/0066; A61K 8/355
USPC .......................................................... 8/405
See application file for complete search history.

(56) References Cited

U.S. PATENT DOCUMENTS

| | | | |
|---|---|---|---|
| 3,787,174 A | 1/1974 | Kalopissis et al. | |
| 3,792,090 A | 2/1974 | Kalopissis et al. | |
| 3,817,699 A | 6/1974 | Kalopissis et al. | |
| 3,853,464 A | 12/1974 | Kalopissis et al. | |
| 3,867,094 A | 2/1975 | Kalopissis et al. | |
| 3,884,625 A | 5/1975 | Kalopissis et al. | |
| 3,894,837 A | 7/1975 | Kalopissis et al. | |
| 3,905,761 A | 9/1975 | Kalopissis et al. | |
| 3,919,265 A * | 11/1975 | Bugaut et al. | 552/306 |
| 3,929,404 A | 12/1975 | Kalopissis et al. | |
| 3,953,508 A | 4/1976 | Kalopissis et al. | |
| 3,972,937 A | 8/1976 | Kalopissis et al. | |
| 4,003,699 A | 1/1977 | Rose et al. | |
| 4,042,627 A | 8/1977 | Kalopissis et al. | |
| 4,054,147 A | 10/1977 | Kalopissis et al. | |
| 4,112,229 A | 9/1978 | Kalopissis et al. | |
| RE30,199 E | 1/1980 | Rose et al. | |
| 4,222,958 A | 9/1980 | Kalopissis et al. | |
| 4,260,749 A * | 4/1981 | Bugaut et al. | 544/166 |

(Continued)

FOREIGN PATENT DOCUMENTS

| | | | | |
|---|---|---|---|---|
| CH | 581996 | * | 11/1976 | A61K 7/13 |
| CH | 581996 A5 | | 11/1976 | |

(Continued)

OTHER PUBLICATIONS

STIC Search Report dated Feb. 25, 2015.*

(Continued)

*Primary Examiner* — Eisa Elhilo
(74) *Attorney, Agent, or Firm* — The Marbury Law Group, PLLC

(57) ABSTRACT

The present invention relates to quinone direct dyes of formula (I) below, organic or mineral acid or base salts thereof, tautomeric forms, optical isomers or geometrical isomers thereof and/or solvates thereof: and also to the use thereof for dyeing keratin fibers, in particular human keratin fibers such as the hair. The invention also relates to a composition for dyeing keratin fibers, comprising such direct dyes in a suitable dyeing medium. Similarly, a subject of the present invention is a process for dyeing keratin fibers, using the said dye composition.

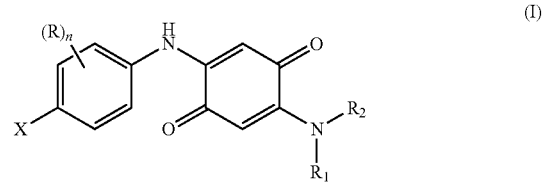

16 Claims, No Drawings

(56) References Cited

U.S. PATENT DOCUMENTS

| | | | |
|---|---|---|---|
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Mockli |
| 5,766,576 | A | 6/1998 | Lowe et al. |
| 6,099,592 | A | 8/2000 | Vidal et al. |
| 6,338,741 | B1 | 1/2002 | Vidal et al. |
| 6,645,258 | B2 | 11/2003 | Vidal et al. |
| 6,730,789 | B1 | 5/2004 | Birault et al. |
| 8,066,782 | B2 | 11/2011 | Leduc et al. |
| 2002/0050013 | A1 | 5/2002 | Vidal et al. |
| 2003/0019051 | A9 | 1/2003 | Vidal et al. |
| 2011/0041263 | A1 | 2/2011 | Leduc et al. |

FOREIGN PATENT DOCUMENTS

| | | | |
|---|---|---|---|
| DE | 2359399 | A1 | 6/1975 |
| DE | 3843892 | A1 | 6/1990 |
| DE | 4133957 | A1 | 4/1993 |
| DE | 19543988 | A1 | 5/1997 |
| EP | 0714954 | A2 | 6/1996 |
| EP | 0770375 | A1 | 5/1997 |
| FR | 2047932 | | 3/1971 |
| FR | 2056799 | | 5/1971 |
| FR | 2106661 | | 5/1972 |
| FR | 2121101 | | 8/1972 |
| FR | 2165965 | | 8/1973 |
| FR | 2189380 | | 1/1974 |
| FR | 2234277 | | 1/1975 |
| FR | 2262023 | | 9/1975 |
| FR | 2733749 | A1 | 11/1996 |
| FR | 2801308 | A1 | 5/2001 |
| FR | 2886136 | A1 | 12/2006 |
| FR | 2925049 | A1 | 6/2009 |
| GB | 1026978 | A | 4/1966 |
| GB | 1153196 | A | 5/1969 |
| JP | 02019576 | | 1/1990 |
| JP | 05163124 | | 6/1993 |
| WO | 9408969 | A1 | 4/1994 |
| WO | 9408970 | A1 | 4/1994 |
| WO | 9501772 | A1 | 1/1995 |
| WO | 9515144 | A1 | 6/1995 |
| WO | 9615765 | A1 | 5/1996 |
| WO | 2010142777 | A1 | 12/2010 |
| WO | 2013087772 | A1 | 6/2013 |

OTHER PUBLICATIONS

International Search Report for International Application No. PCT/EP2012/075386, published as WO 2013/087770, (Jan. 2013).

International Search Report for International Application No. PCT/EP2012/075388, published as WO 2013/087772, (Mar. 2013).

English language abstract for EP 0770375, (1997).

English language abstract for EP 1728500 (related to FR 2886136), (2006).

English language abstract for JP 02-019576, (1990).

English language abstract for JP 05-163124.

\* cited by examiner

PARTICULAR QUINONE DIRECT DYES, DYE COMPOSITION COMPRISING AT LEAST ONE SUCH DYE, IMPLEMENTATION PROCESS THEREFOR AND USE THEREOF

CROSS REFERENCE TO RELATED APPLICATIONS

This is a national stage application of PCT/EP2012/075386, filed internationally on Dec. 13, 2012, which claims priority to U.S. Provisional Application No. 61/584,996, filed on Jan. 10, 2012, as well as French Application No. 1161575, filed Dec. 13, 2011, all of which are incorporated herein by their entireties.

The present invention relates to particular quinone direct dyes and also to the use thereof for dyeing keratin fibres, in particular human keratin fibres such as the hair.

The invention also relates to a composition for dyeing keratin fibres comprising such quinone direct dyes in a suitable dyeing medium, and also to a dyeing process using the said composition.

Specifically, a subject of the invention is precursors of these direct dyes, their use for dyeing fibres and a multi-compartment device containing them.

The present invention relates to the field of dyeing keratin fibres and more particularly to the field of hair dyeing.

It is known practice to dye keratin fibres, and in particular the hair, with dye compositions containing one or more direct dyes, according to a "direct dyeing" process.

The process conventionally used in direct dyeing consists in applying to keratin fibres one or more direct dyes, or colouring molecules, which have affinity for the said fibres, leaving them to stand on the fibres, and then rinsing the fibres. The direct dyes used hitherto are generally nitrobenzene dyes, anthraquinone dyes, nitropyridine dyes, dyes of azo, xanthene, acridine or azine type or triarylmethane-based dyes.

These direct dyes may also be applied to keratin fibres in the presence of an oxidizing agent if it is desired to obtain simultaneous lightening of the fibres.

However, the colorations resulting therefrom are temporary or semi-permanent since the nature of the interactions that bind the direct dyes to the keratin fibre and their desorption from the surface and/or the core of the fibre are responsible for their weak dyeing power and their poor fastness with respect to washing, inclement weather or perspiration.

These dyes also have the drawback of lacking stability towards light, on account of the poor resistance of the chromophore to photochemical attack, which has a tendency to lead to fading over time of the coloration of keratin fibres.

There is thus a real need for direct dyes that can not only dye keratin fibres satisfactorily, but that are also stable towards light, and are capable of giving colorations that are resistant to the various attacking factors to which the fibres may be subjected, such as bad weather, washing and perspiration.

These aims are achieved with the present invention, one subject of which is especially quinone direct dyes of formula (I) below, organic or mineral acid or base salts thereof, tautomeric forms, optical isomers or geometrical isomers thereof and/or solvates thereof:

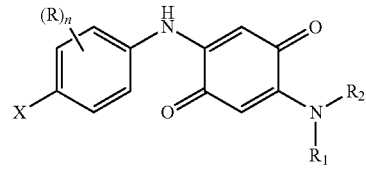

in which formula (I):
n represents an integer equal to 0, 1, 2, 3 or 4;
R represents:
 a linear or branched $C_1$-$C_4$ alkyl radical;
 a linear or branched $C_1$-$C_4$ alkyl radical, substituted with one or more identical or different radicals chosen from hydroxyl and imidazolium radicals, $An^-$; $An^-$ denoting a cosmetically acceptable anion or mixture of anions;
 a $C_1$-$C_4$ alkoxy radical;
 a halogen atom;
$R_1$ represents:
 a linear or branched $C_1$-$C_5$ alkyl radical;
 a linear or branched $C_1$-$C_5$ alkyl radical, optionally substituted with one or more hydroxyl radicals;
$R_2$ represents:
 a linear or branched $C_1$-$C_5$ alkyl radical;
 a linear or branched $C_1$-$C_5$ alkyl radical, optionally substituted with one or more hydroxyl radicals;
X represents:
 a hydroxyl radical;
 a radical —$NR_3R_4$ in which $R_3$ and $R_4$ represent, independently of each other:
  a hydrogen atom;
  a linear or branched $C_1$-$C_6$ alkyl radical;
  a linear or branched $C_1$-$C_6$ alkyl radical, substituted with one or more hydroxyl or $C_1$-$C_4$ alkoxy radicals.

Another subject of the present invention concerns the use of one or more quinone direct dyes of formula (I) as defined previously for the dyeing of keratin fibres, in particular human keratin fibres such as the hair.

The present invention also relates to a composition for dyeing keratin fibres, in particular human keratin fibres such as the hair, comprising, in a suitable dyeing medium, one or more quinone direct dyes of formula (I) as defined previously.

In particular, the invention also relates to the use of the said dye composition for dyeing keratin fibres, especially human keratin fibres such as the hair.

The invention also relates to a process for dyeing keratin fibres, in particular human keratin fibres such as the hair, in which the said dye composition according to the invention is applied to the said fibres for a time that is sufficient to obtain the desired coloration, after which the resulting fibres are rinsed, optionally washed with shampoo, rinsed again and dried or left to dry.

Similarly, the invention relates more particularly to a process for lightening keratin fibres, in particular human keratin fibres such as the hair, in which (i) the said dye composition, free of oxidizing agent, and (ii) a cosmetic composition comprising one or more oxidizing agents are applied to the said fibres; compositions (i) and (ii) being applied to the said keratin fibres sequentially or simultaneously for a time that is sufficient to obtain the desired lightening, after which the fibres are rinsed, optionally washed with shampoo and rinsed again, and the resulting fibres are dried or left to dry.

The quinone direct dyes of formula (I) according to the invention can thus give colorations that are resistant to the various attacking factors to which keratin fibres may be subjected, such as inclement weather, light, washing and perspiration.

Furthermore, the direct dyes according to the invention can satisfactorily dye keratin fibres, especially producing powerful, chromatic, sparingly selective colorations and lead to an improved uptake of the colouration.

The direct dyes according to the invention have the advantage of being light-fast and can be used in the presence of an oxidizing agent, which facilitates their use in lightening direct dyeing compositions based on oxidizing agents.

In other words, the direct dyes according to the present invention lead to fast colorations and are compatible with dye compositions intended for lightening keratin fibres.

Moreover, a subject of the invention is colourless or weakly coloured compounds of leuco type, which are the reduced form of the quinone direct dyes according to the invention of formula (II) below, organic or mineral acid or base salts thereof, tautomeric forms, optical isomers or geometrical isomers thereof, and/or solvates thereof:

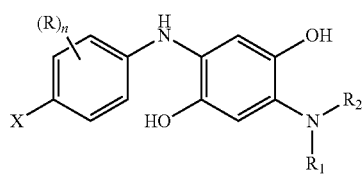

(II)

in which formula (II) n, R, $R_1$, $R_2$ and X have the same meanings as those indicated in formula (I).

The compounds of leuco type according to the invention lead, in the presence of one or more oxidizing agents, to the quinone direct dyes of formula (I).

Thus, the invention also relates to the use of one or more compounds of leuco type of formula (II) as precursors of the direct dyes of formula (I).

In particular, the invention relates to the use of one or more compounds of leuco type of formula (II) in the presence of one or more oxidizing agents, for dyeing keratin fibres, in particular human keratin fibres such as the hair.

The present invention also relates to a multi-compartment device or "kit" containing a first compartment comprising a cosmetic composition comprising one or more compounds of leuco type of formula (II) as defined previously, and a second compartment comprising one or more oxidizing agents.

The compounds of leuco type of formula (II) used under oxidizing conditions thus have the advantage of giving colorations that are resistant to the various attacking factors to which keratin fibres may be subjected, such as inclement weather, washing, light and perspiration.

Other characteristics, aspects, subjects and advantages of the present invention will emerge even more clearly on reading the description and the examples that follow.

I. Quinone Direct Dyes

Preferably, in formula (I), quinone direct dyes according to the invention are such that, taken together or separately:
n represents an integer equal to 0, 1 or 2;
R represents:
a linear or branched $C_1$-$C_4$ alkyl radical, preferably methyl;
a $C_1$-$C_4$ alkoxy radical, preferably a methoxy radical;
a halogen atom, preferably chlorine;

$R_1$ represents:
a linear or branched $C_1$-$C_5$ alkyl radical, preferably a methyl or ethyl radical;
a linear or branched $C_1$-$C_5$ alkyl radical, substituted with one or more hydroxyl radicals, preferably a 2-hydroxyethyl radical;
$R_2$ represents:
a linear or branched $C_1$-$C_5$ alkyl radical, preferably a methyl or ethyl radical;
a linear or branched $C_1$-$C_5$ alkyl radical, substituted with one or more hydroxyl radicals, preferably a 2-hydroxyethyl radical; and/or
X represents:
a hydroxyl radical;
a radical —$NR_3R_4$ in which $R_3$ and $R_4$ represent, independently of each other:
a hydrogen atom;
a linear or branched $C_1$-$C_6$ alkyl radical;
a linear or branched $C_1$-$C_6$ alkyl radical, substituted with one or more hydroxyl radicals.

An⁻ denotes a cosmetically acceptable anion or mixture of anions, for instance halides, such as chloride, methosulfates, nitrates; alkylsulfonates: Alk-S(O)$_2$O⁻ such as methanesulfonate or mesylate, and ethanesulfonate; arylsulfonates: Ar—S(O)$_2$O⁻ such as benzenesulfonate and toluenesulfonate or tosylate; citrate; succinate; tartrate; lactate; alkyl sulfates: Alk-O—S(O)O⁻ such as methylsulfate; arylsulfates such as benzenesulfate and toluenesulfate; phosphate; acetate; triflate; and borates such as tetrafluoroborate.

Preferably, An⁻ is an anionic counterion chosen from bromide, chloride, and methylsulfate and toluenesulfonate ions or a mixture of these ions.

Preferably, n represents an integer equal to 0, 1 or 2, and more particularly n is equal to 0 or 2.

Preferably, R represents a linear or branched $C_1$-$C_4$ alkyl radical, a $C_1$-$C_4$ alkoxy radical or a halogen atom. More preferentially, R is chosen from a methyl radical, a methoxy radical and a chlorine atom.

Preferably, $R_1$ represents a linear or branched $C_1$-$C_5$ alkyl radical and $R_2$ represents a linear or branched $C_1$-$C_5$ alkyl radical, substituted with one or more hydroxyl radicals, or vice versa.

More preferentially, $R_1$ is chosen from a methyl radical and an ethyl radical, and $R_2$ is a 2-hydroxyethyl radical, or vice versa.

Preferably, X represents a hydroxyl radical.

As a variant, X represents a radical —$NR_3R_4$ in which $R_3$ and $R_4$ represent, independently of each other, a hydrogen atom or a linear or branched $C_1$-$C_6$ alkyl radical, optionally substituted with one or more hydroxyl radicals.

Preferably, $R_3$ and $R_4$ represent, independently of each other, a hydrogen atom or a methyl, ethyl, isopropyl or 2-hydroxyethyl radical.

According to one embodiment, n represents an integer equal to 0, 1 or 2 and $R_1$ represents a linear or branched $C_1$-$C_5$ alkyl radical and $R_2$ represents a linear or branched $C_1$-$C_5$ alkyl radical, substituted with one or more hydroxyl radicals, or vice versa.

In accordance with this embodiment, n is preferably equal to 2, $R_1$ is chosen from a methyl radical and an ethyl radical, and $R_2$ is a 2-hydroxyethyl radical, or vice versa.

In particular, n is equal to 2, R represents a linear or branched $C_1$-$C_4$ alkyl radical or a $C_1$-$C_4$ alkoxy radical and $R_1$ is chosen from a methyl radical and an ethyl radical and $R_2$ is a 2-hydroxyethyl radical, or vice versa.

According to another embodiment, n is equal to 0 and $R_1$ represents a linear or branched $C_1$-$C_5$ alkyl radical and $R_2$ represents a linear or branched $C_1$-$C_5$ alkyl radical, substituted with one or more hydroxyl radicals, or vice versa.

According to another embodiment, n is equal to 1 and $R_1$ represents a linear or branched $C_1$-$C_5$ alkyl radical and $R_2$ represents a linear or branched $C_1$-$C_5$ alkyl radical, substituted with one or more hydroxyl radicals, or vice versa.

Preferably, the quinone direct dyes of formula (I) according to the invention are chosen from the following compounds and the geometrical or optical isomer forms thereof, the tautomers thereof, the organic or mineral acid or base salts thereof or the solvates thereof such as hydrates:

Compound 1

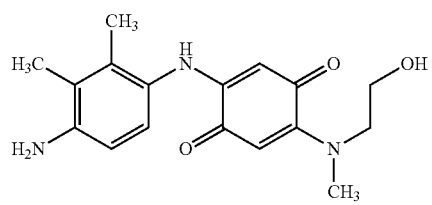

2-(4-Amino-2,3-dimethylphenylamino)-5-[(2-hydroxyethyl)methylamino][1,4]benzoquinone Compound 2

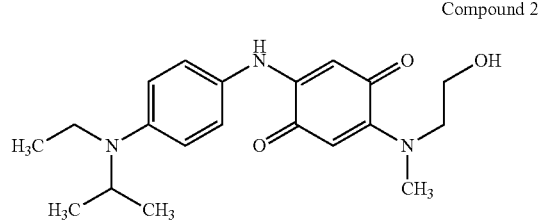

2-[4-(Ethylisopropylamino)phenylamino]-5-[(2-hydroxyethyl)methylamino][1,4]benzoquinone Compound 3

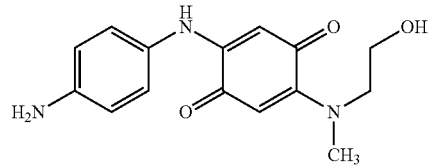

2-(4-Aminophenylamino)-5-[(2-hydroxyethyl)methylamino][1,4]benzoquinone

Compound 4

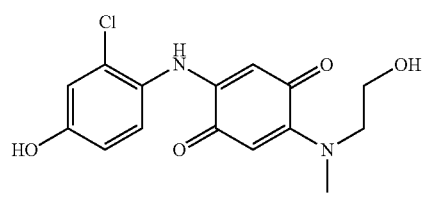

2-(2-Chloro-4-hydroxyphenylamino)-5-[(2-hydroxyethyl)methylamino][1,4]benzoquinone Compound 5

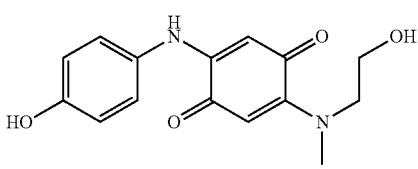

2-[(2-Hydroxyethyl)methylamino]-5-(4-hydroxyphenylamino)[1,4]benzoquinone

Compound 6

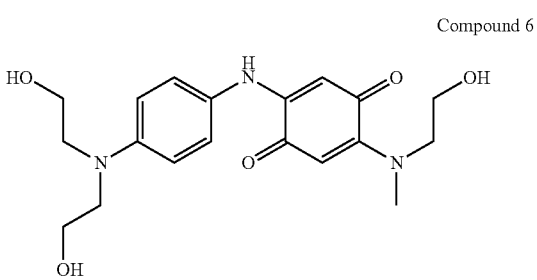

2-{4-[Bis(2-hydroxyethyl)amino]phenylamino}-5-[(2-hydroxyethyl)methylamino][1,4]benzoquinone Compound 7

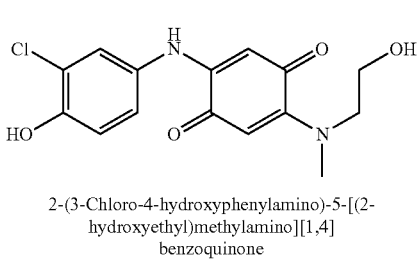

2-(3-Chloro-4-hydroxyphenylamino)-5-[(2-hydroxyethyl)methylamino][1,4]benzoquinone Compound 8

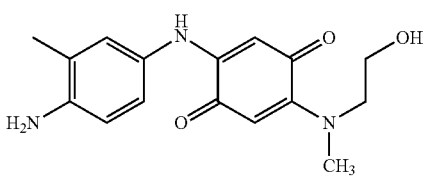

2-(4-Amino-3-methylphenylamino)-5-[(2-hydroxyethyl)methylamino][1,4]benzoquinone Compound 9

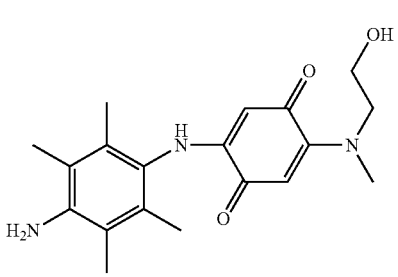

2-(4-Amino-2,3,5,6-tetramethylphenylamino)-5-[(2-hydroxyethyl)methylamino][1,4]benzoquinone -continued Compound 10

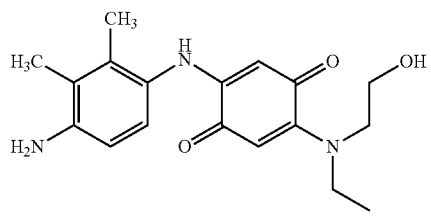

2-(4-Amino-2,3-dimethylphenylamino)-
5-[(2-hydroxyethyl)ethylamino][1,4]
benzoquinone Compound 11

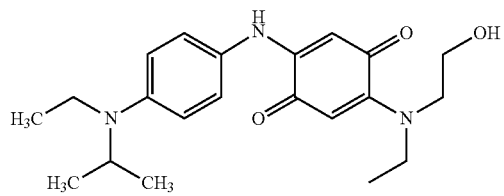

2-[4-(Ethylisopropylamino)phenylamino]-
5-[(2-hydroxyethyl)ethylamino][1,4]
benzoquinone Compound 12

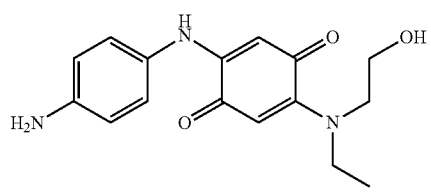

2-(4-(Aminophenylamino)-5-[(2-
hydroxyethyl)ethylamino][1,4]
benzoquinone

Compound 13

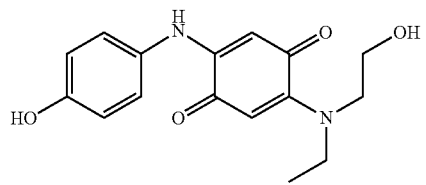

2-[(2-Hydroxyethyl)ethylamino]-
5-(4-hydroxyphenylamino)[1,4]
benzoquinone

Compound 14

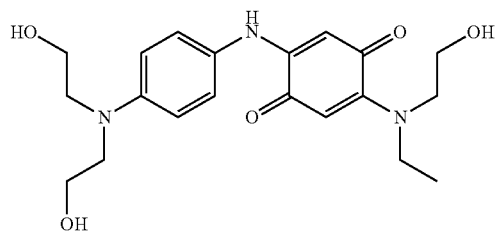

2-{4-[Bis(2-hydroxyethyl)amino]phenylamino}-
5-[(2-hydroxyethyl)
ethylamino][1,4]
benzoquinone Compound 15

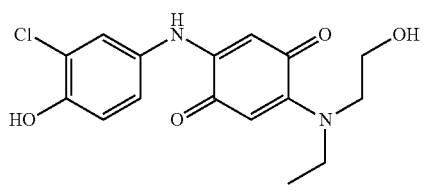

2-(3-Chloro-4-hydroxyphenylamino)-5-[(2-
hydroxyethyl)ethylamino][1,4]
benzoquinone Compound 16

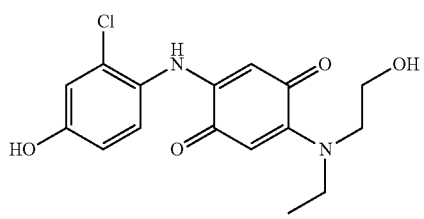

2-(2-Chloro-4-hydroxyphenylamino)-5-[ethyl-(2-
hydroxyethyl)amino][1,4]
benzoquinone Compound 17

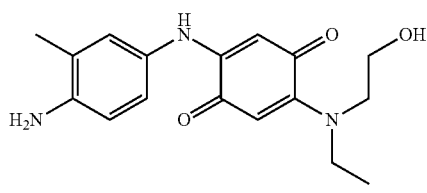

2-(4-Amino-3-methylphenylamino)-5-[(2-
hydroxyethyl)ethylamino][1,4]
benzoquinone Compound 18

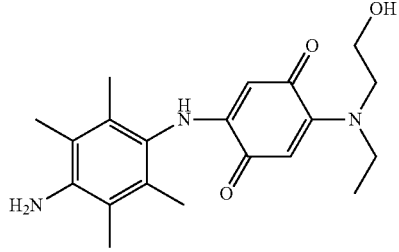

2-(4-Amino-2,3,5,6-tetramethylphenylamino)-
5-[(2-hydroxyethyl)ethylamino][1,4]
benzoquinone Compound 19

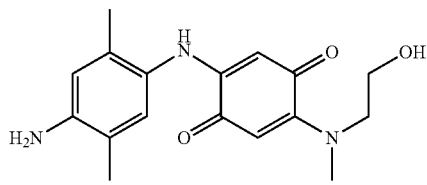

2-(4-Amino-2,5-dimethylphenylamino)-
5-[(2-hydroxyethyl)methylamino][1,4]
benzoquinone -continued Compound 20

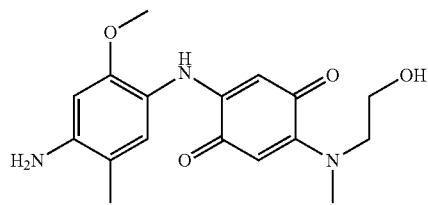

2-(4-Amino-2-methoxy-5-methylphenylamino)-5-[(2-hydroxyethyl)methylamino][1,4]benzoquinone Compound 21

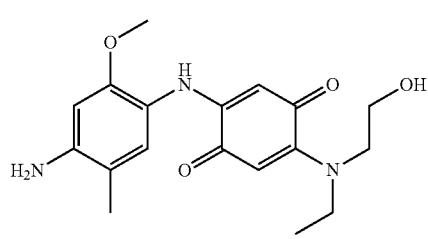

2-(4-Amino-2-methoxy-5-methylphenylamino)-5-[ethyl-(2-hydroxyethyl)amino][1,4]benzoquinone Compound 22

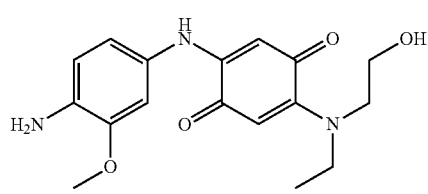

2-(4-Amino-3-methoxyphenylamino)-5-[ethyl-(2-hydroxyethyl)amino][1,4]benzoquinone Compound 23

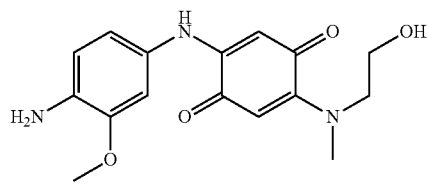

2-(4-Amino-3-methoxyphenylamino)-5-[(2-hydroxyethyl)methylamino][1,4]benzoquinone Compound 24

2-(4-Hydroxy-3,5-dimethylphenylamino)-5-[(2-hydroxyethyl)methylamino][1,4]benzoquinone -continued Compound 25

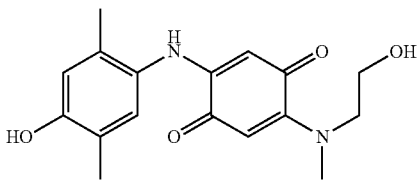

2-(4-Hydroxy-2,5-dimethylphenylamino)-5-[(2-hydroxyethyl)methylamino][1,4]benzoquinone Compound 26

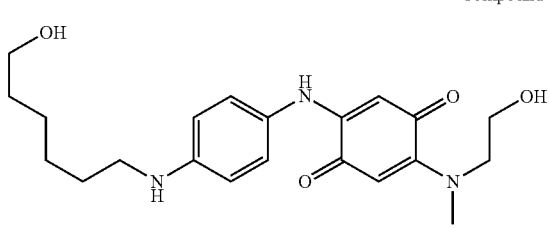

2-[(2-Hydroxyethyl)methylamino]-5-[4-(6-hydroxy-hexylamino)phenylamino][1,4]benzoquinone Compound 27

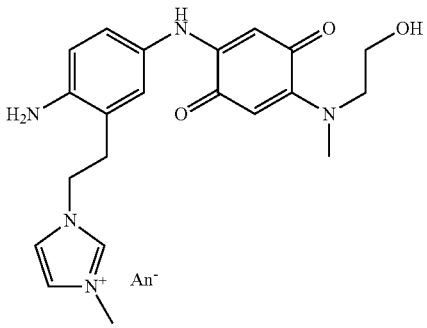

3-[2-(2-Amino-5-{4-[(2-hydroxyethyl)methylamino]-3,6-dioxocyclohexa-1,4-dienylamino}phenyl)ethyl]-1-methyl-3H-imidazol-1-ium with An- as defined previously Compound 28

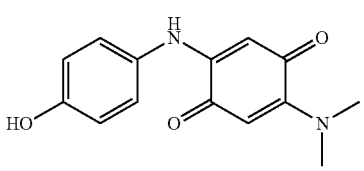

2-Dimethylamino-5-(4-hydroxyphenylamino)[1,4]benzoquinone

Compound 29

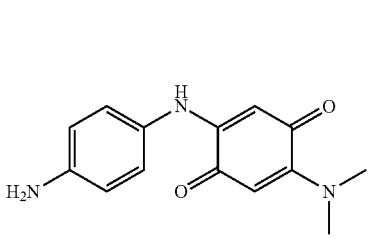

2-(4-Aminophenylamino)-5-dimethylamino[1,4]benzoquinone

-continued

Compound 30

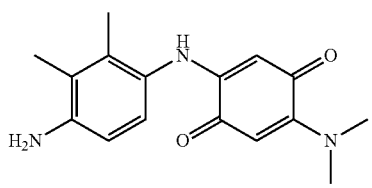

2-(4-Amino-2,3-dimethylphenylamino)-5-dimethylamino)[1,4]benzoquinone

Compound 31

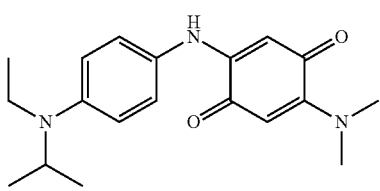

2-Dimethylamino-5-[4-(ethylisopropylamino)phenyl-amino][1,4]benzoquinone

Compound 32

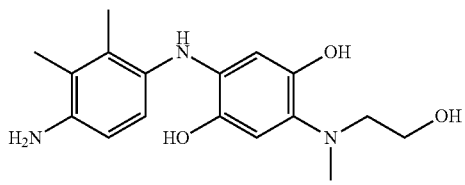

2-[(4-amino-2,3-dimethylphenyl)amino]-5-[(2hydroxyethyl)(methyl)amino]benzene-1,4-diol Compound 33

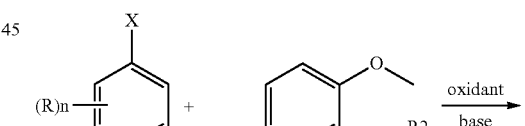

2-(4-amino-2,5-dimethylphenylamino)-5-[(2-hydroxyethyl)methylamino][1,4]benzene-1,4-diol Preferably, the direct dyes of formula (I) according to the present invention are chosen from the quinone direct dyes 1, 2, 3, 4, 5, 6, 7, 8, 9, 10, 11, 19, 20, 21, 22, 23, 24, 25, 32 and 33.

Even more preferably, the quinone direct dyes of formula (I) according to the invention are chosen from the quinone direct dyes 1, 2, 3, 4, 7, 10, 11 and 32.

The quinone direct dyes of formula (I) may be obtained according to the procedure described below:

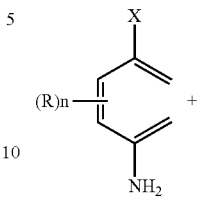

1a

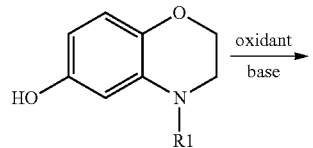

2

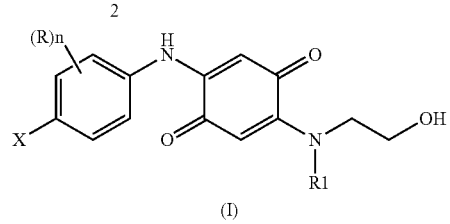

(I)

The compounds corresponding to formula (I) are generally obtained by reacting the derivatives 1a with the morpholine derivatives 2 in basic medium in the presence of an oxidizing agent. The base used is preferentially an aqueous solution of ammonia or of sodium hydroxide and the oxidizing agent is preferentially chosen from hydrogen peroxide, potassium ferricyanide, air, ammonium persulfate and manganese oxide.

Synthetic approaches similar to that described previously are described in patents FR 2 234 277, FR 2 047 932, FR 2 106 661 and FR 2 121 101.

The quinone direct dyes of formula (I) may also be obtained according to the procedure as described below:

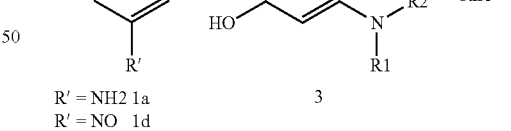

R' = NH2  1a
R' = NO   1d

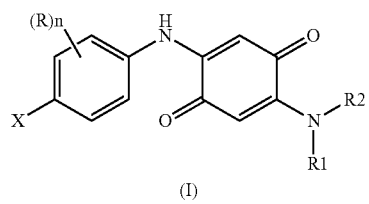

(I)

The compounds corresponding to formula (I) are generally obtained by reacting the derivatives 1a or 1d with the meta-aminophenols 3 in basic medium in the presence of an oxidizing agent. The base used is preferentially an aqueous solution of ammonia or of sodium hydroxide and the oxidizing agent is preferentially chosen from hydrogen peroxide, potassium ferricyanide, air, ammonium persulfate and manganese oxide.

Similar synthetic approaches are described in patent application FR 21189380.

The invention also relates to the use of one or more quinone direct dyes of formula (I) as described previously for dyeing keratin fibres, in particular human keratin fibres such as the hair.

II. Dye Composition

The present invention also relates to a composition for dyeing keratin fibres, in particular human keratin fibres such as the hair, comprising, in a suitable dyeing medium, one or more direct dyes of formula (I) as defined previously.

Preferably, the dye composition comprises one or more quinone direct dyes of formula (I) chosen from compounds 1, 2, 3, 4, 5, 6, 7, 8, 9, 10, 11, 19, 20, 21, 22, 23, 24, 25, 32 and 33, and also mixtures thereof.

Even more preferentially, the dye composition comprises one or more quinone direct dyes of formula (I) chosen from compounds 1, 2, 3, 4, 7, 10, 11 and 32, and mixtures thereof.

The direct dye(s) as defined previously may be present in the dye composition according to the invention in a content ranging from 0.001% to 10% by weight and preferably in a content ranging from 0.005% to 6% by weight, relative to the total weight of the dye composition.

The dye composition of the invention may also comprise one or more oxidation dyes.

The oxidation dyes are generally chosen from oxidation bases optionally combined with one or more couplers.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloro aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and addition salts thereof with an acid.

Preference is particularly given, among the abovementioned para-phenylenediamines, to para-phenylenediamine, para-tolylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their addition salts with an acid.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in patents GB 1 026 978 and GB 1 153 196, such as 2,5-diaminopyridine, 2-(4-methoxyphenyl)amino-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyrid-5-yl, 3-aminopyrazolo[1,5-a]pyrid-4-ol, 3-aminopyrazolo[1,5-a]pyrid-6-ol, 3-aminopyrazolo[1,5-a]pyrid-7-ol and their addition salts.

Mention may be made, among pyrimidine derivatives, of the compounds described, for example, in Patents DE 2359399, JP 63-169571, JP 05-163124, and EP 0 770 375 or Patent Application WO 96/15765, such as 2,4,5,6-tetraaminopyrimidine, 4-hydroxy-2,5,6-15 triaminopyrimidine, 2-hydroxy-4,5,6-triaminopyrimidine, 2,4dihydroxy-5,6-diaminopyrimidine, 2,5,6-triaminopyrimidine and their addition salts and their tautomeric forms, when a tautomeric equilibrium exists.

Mention may be made, among pyrazole derivatives, of the compounds described in patents DE 3843892 and DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole and their addition salts. 4,5-Diamino-1-(β-methoxyethyl)pyrazole may also be used.

Use will preferably be made of a 4,5-diaminopyrazole and even more preferentially of 4,5-diamino-1-(β-hydroxyethyl)pyrazole and/or a salt thereof.

Mention may also be made, as pyrazole derivatives, of diamino-N,N-dihydropyrazolopyrazolones and in particular those described in application FR-A-2 886 136, such as the following compounds and their addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or one of its salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or one of their salts.

The dye composition may optionally comprise one or more couplers advantageously chosen from those conventionally used for the dyeing of keratin fibres.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers which can be used in the context of the invention are chosen in particular from the addition salts with an acid, such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight and preferably from 0.005% to 6% by weight relative to the total weight of the composition.

The content of coupler(s), if they are present, each advantageously represent from 0.001% to 10% by weight relative to the total weight of the composition, and preferably from 0.005% to 6% by weight relative to the total weight of the dye composition.

The dye composition according to the invention may also comprise one or more additional direct dyes other than the quinone direct dyes according to the present invention.

The additional direct dye(s) according to the invention are chosen from neutral, acidic or cationic nitrobenzene dyes, neutral, acidic or cationic azo direct dyes, neutral, acidic or cationic quinone and in particular anthraquinone direct dyes other than those of the present invention, azine direct dyes, triarylmethane direct dyes, azomethine direct dyes and natural direct dyes.

Among the benzenic direct dyes that may be used according to the invention, mention may be made in a non-limiting manner of the following compounds:
1,4-diamino-2-nitrobenzene;
1-amino-2-nitro-4-β-hydroxyethylaminobenzene;
1-amino-2-nitro-4-bis(β-hydroxyethyl)aminobenzene;
1,4-bis(β-hydroxyethylamino)-2-nitrobenzene;
1-β-hydroxyethylamino-2-nitro-4-bis(β-hydroxyethylamino)benzene;
1-β-hydroxyethylamino-2-nitro-4-aminobenzene;
1-β-hydroxyethylamino-2-nitro-4-(ethyl)(β-hydroxyethyl)aminobenzene;
1-amino-3-methyl-4-β-hydroxyethylamino-6-nitrobenzene;
1-amino-2-nitro-4-β-hydroxyethylamino-5-chlorobenzene;
1,2-diamino-4-nitrobenzene;
1-amino-2-β-hydroxyethylamino-5-nitrobenzene;
1,2-bis(β-hydroxyethylamino)-4-nitrobenzene;
1-amino-2-tris(hydroxymethyl)methylamino-5-nitrobenzene;
1-hydroxy-2-amino-5-nitrobenzene;
1-hydroxy-2-amino-4-nitrobenzene;
1-hydroxy-3-nitro-4-aminobenzene;
1-hydroxy-2-amino-4,6-dinitrobenzene;
1-β-hydroxyethyloxy-2-β-hydroxyethylamino-5-nitrobenzene;
1-methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropylamino-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-amino ethylamino-5-methoxy-2-nitrobenzene;

1-hydroxy-2-chloro-6-ethylamino-4-nitrobenzene;
1-hydroxy-2-chloro-6-amino-4-nitrobenzene;
1-hydroxy-6-bis(β-hydroxyethyl)amino-3-nitrobenzene;
1-β-hydroxyethylamino-2-nitrobenzene; and
1-hydroxy-4-β-hydroxyethylamino-3-nitrobenzene.

Among the azo direct dyes that may be used according to the invention, mention may be made of the cationic azo dyes described in patent applications WO 95/15144, WO-95/01772 and EP-714954, the content of which forms an integral part of the invention.

Among these compounds, the ones that may be mentioned most particularly are the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes, described in the Colour Index International, 3rd edition: Disperse Red 17, Acid Yellow 9, Acid Black 1, Basic Red 22, Basic Red 76, Basic Red 51, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds:
1-N-methylmorpholiniumpropylamino-4-hydroxyanthraquinone
1-aminopropylamino-4-methylamino anthraquinone
1-aminopropylaminoanthraquinone
5-β-hydroxyethyl-1,4-diamino anthraquinone
2-amino ethylamino anthraquinone
1,4-bis(β,γ-dihydroxypropylamino)anthraquinone.

Among the azine dyes, mention may be made of the following compounds: Basic Blue 17, Basic Red 2.

Among the triarylmethane dyes that may be used according to the invention, mention may be made of the following compounds: Basic Green 1, Acid Blue 9, Basic Violet 3, Basic Violet 14, Basic Blue 7, Acid Violet 49, Basic Blue 26, Acid Blue 7.

Among the azomethine dyes that may be used according to the invention, mention may be made of the following compounds:
2-β-hydroxyethlyamino-5-[bis(β-4'-hydroxyethyl)amino] anilino-1,4-benzoquinone;
2-β-hydroxyethylamino-5-(2'-methoxy-4'-amino)anilino-1,4-benzoquinone;
3-N-(2'-chloro-4'-hydroxy)phenylacetylamino-6-methoxy-1,4-benzoquinone imine;
3-N-(3'-chloro-4'-methylamino)phenylureido-6-methyl-1,4-benzoquinone imine; and
3-[4'-N-(ethyl,carbamylmethyamino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes and in particular henna-based poultices or extracts may also be used.

The additional direct dye(s) may be present in the dye composition in a content ranging from 0.001% to 10% by weight and preferably in a content ranging from 0.005% to 6% by weight, relative to the total weight of the composition.

Preferably, the dye composition comprises one or more quinone direct dyes of formula (I) and one or more azomethine direct dyes.

The medium that is suitable for dyeing, also known as the dye support, is a cosmetic medium generally formed from water or a mixture of water and of at least one organic solvent. Examples of organic solvents that may be mentioned include $C_1$-$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

When they are present, the solvents are present in proportions preferably of between 1% and 99% by weight approximately and even more preferentially between 5% and 95% by weight approximately relative to the total weight of the dye composition.

The dye composition may also contain various adjuvants conventionally used in hair dye compositions, such as anionic, cationic, nonionic or amphoteric surfactants or mixtures thereof, anionic, cationic, nonionic or amphoteric polymers or mixtures thereof, mineral or organic thickeners, and in particular anionic, cationic, nonionic and amphoteric polymeric associative thickeners, antioxidants, penetrants, sequestrants, fragrances, buffers, dispersants, solubilizers, conditioning agents, for instance volatile or non-volatile, modified or unmodified silicones such as amino silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition in accordance with the invention is generally between 3 and 12 approximately, particularly between 5 and 11 approximately and even more particularly from 6 to 9.

Preferably, the pH of the dye composition in accordance with the invention ranges from 9 to 12, more preferably from 9 to 10.

It may be adjusted to the desired value by means of acidifying or basifying agents commonly used in the dyeing of keratin fibres, or alternatively using standard buffer systems.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents that may be mentioned, for example, are aqueous ammonia, alkali metal carbonates, alkanolamines such as monoethanolamine, diethanolamine and triethanolamine, and also derivatives thereof, sodium hydroxide, potassium hydroxide and the compounds of formula (III) below:

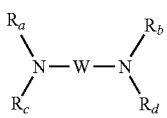

(III)

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels, or in any other form that is suitable for dyeing keratin fibres, and especially human hair.

As indicated previously, the invention also relates to the use of the dye composition as defined previously for dyeing keratin fibres, in particular human keratin fibres such as the hair.

III. Dyeing Process

The dyeing process according to the present invention consists in applying to wet or dry keratin fibres a dye composition as defined previously for a time that is sufficient to obtain the desired coloration, and the fibres are then rinsed, optionally washed with shampoo and rinsed again, and the resulting fibres are dried or left to dry.

Preferably, the leave-on time for the dye composition is between 1 and 60 minutes, preferably between 5 and 40 minutes and even more preferably between 10 and 30 minutes.

The dye composition is generally applied to the keratin fibres at room temperature, preferably between 25 and 55° C.

According to one embodiment, the dye composition according to the invention is applied to the keratin fibres in the presence of one or more oxidizing agents for a time that is sufficient to obtain the desired lightening.

The oxidizing agent may be present in the dye composition or may be used separately in a cosmetic composition.

Preferably, the oxidizing agent is used separately in a cosmetic composition.

Thus, the present invention also relates to a process for lightening keratin fibres, in particular human keratin fibres such as the hair, in which (i) the dye composition as defined previously, free of oxidizing agent, and (ii) a cosmetic composition comprising one or more oxidizing agents are applied to the said fibres; compositions (i) and (ii) being applied to the said keratin fibres sequentially or simultaneously for a time that is sufficient to obtain the desired lightening, and the fibres are then rinsed, optionally washed with shampoo and rinsed again, and the resulting fibres are dried or left to dry.

The purposes of the present invention, the term "sequentially" means that the oxidizing composition is applied before or after the dye composition, i.e. as a pretreatment or a post-treatment.

The oxidizing agents used are chosen from hydrogen peroxide, urea peroxide, alkali metal bromates, persalts such as perborates and persulfates, peracids, and oxidase enzymes (with the possible cofactors thereof), among which mention may be made of peroxidases, 2-electron oxidoreductases such as uricases, and 4-electron oxygenases, for instance laccases.

The oxidizing agent is preferably hydrogen peroxide.

The oxidizing composition may also contain various adjuvants conventionally used in compositions for dyeing the hair and as defined previously.

The pH of the oxidizing composition containing the oxidizing agent is such that, after mixing with the dye composition, the pH of the resulting composition applied to the keratin fibres preferably ranges between 3 and 12 approximately, even more preferentially between 5 and 11 and even more particularly between 6 and 8.5. It may be adjusted to the desired value by means of acidifying or basifying agents usually used in the dyeing of keratin fibres and as defined previously.

IV. Compound of Leuco Type

The present invention also relates to compounds of leuco type of formula (II) below, organic or mineral acid or base salts thereof, tautomeric forms, optical isomers or geometrical isomers thereof and/or solvates thereof:

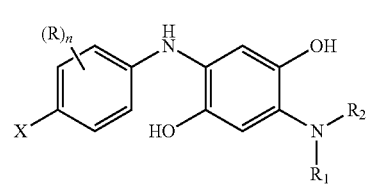

(II)

in which n, R, $R_1$, $R_2$ and X have the same meanings as those indicated in formula (I).

In particular, the preferred variants of n, R, $R_1$, $R_2$ and X in formula (II) of the compounds of leuco type correspond to those indicated in formula (I) of the direct dyes.

The compounds of leuco type corresponding to formula (II) are generally obtained by reacting the compounds of quinone type of formula (I) with a reducing agent according to the reaction scheme below:

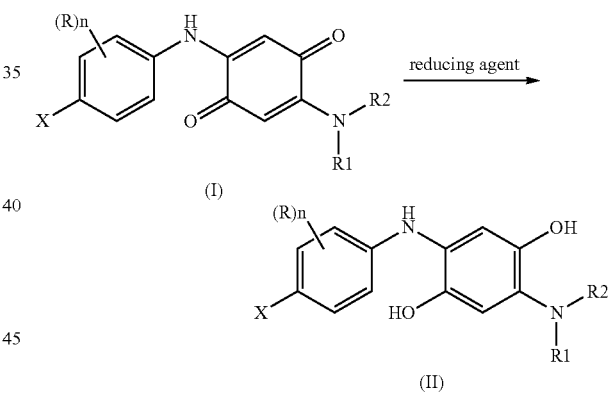

Synthetic approaches similar to this scheme are described in patent applications FR 2 056 799, FR 2 047 932, FR 2 165 965 and FR 2 262 023.

The compounds of leuco type of formula (II) are used as precursors of the direct dyes of formula (I).

Preferably, the compounds of leuco type of formula (II) are chosen from the compounds corresponding to the reduced form of the quinone direct dyes 1 to 33 mentioned previously.

In other words, the compounds of leuco type of formula (II) are chosen from the precursors of the quinone direct dyes 1 to 33.

Even more preferentially, the compounds of leuco type of formula (II) are chosen from precursors of the direct dyes 1, 2, 3, 4, 5, 6, 7, 8, 9, 10, 11, 19, 20, 21, 22, 23, 24, 25, 32 and 33 and preferentially the precursors of the quinone direct dyes 1, 2, 3, 4, 7, 10, 11 and 32.

In particular, the invention relates to a cosmetic composition comprising one or more compounds of leuco type of formula (II) as defined previously.

The present invention also relates to a dyeing process in which a cosmetic composition comprising one or more compounds of leuco type of the abovementioned formula (II) is applied to keratin fibres in the presence of one or more oxidizing agents for a time that is sufficient to develop the desired coloration, after which the fibres are rinsed, optionally washed with shampoo and rinsed again, and the resulting fibres are dried or left to dry.

The oxidizing agent may be atmospheric oxygen or may be chosen from the oxidizing agents mentioned previously.

In particular, when the oxidizing agent is atmospheric oxygen, simple exposure to air of the keratin fibres treated with the composition comprising the compound(s) of leuco type makes it possible to generate the colouring species and, consequently, to colour the fibres.

According to one variant, the oxidizing agent(s) may be applied simultaneously or sequentially to the cosmetic composition comprising the compounds of leuco type.

Thus, the cosmetic composition comprising the oxidizing agent(s) may be applied to the keratin fibres before, simultaneously with or after the cosmetic composition comprising the compounds of leuco type of formula (II) according to the invention.

According to another variant, a ready-to-use composition which results from the mixing of a cosmetic composition comprising one or more compounds of leuco type of the abovementioned formula (II) and of a cosmetic composition comprising one or more oxidizing agents is applied to the keratin fibres.

According to one embodiment, the invention relates to a composition, in particular for dyeing keratin fibres such as the hair, comprising one or more compounds of formula (II) as defined previously and optionally comprising one or more oxidizing agents.

The ready-to-use composition that is thus applied to the keratin fibres may be in various forms, such as in the form of liquids, creams or gels, or in any other form that is suitable for dyeing keratin fibres, and in particular human hair.

The leave-on time for the composition(s) ranges from 1 to 60 minutes, preferably from 5 to 40 minutes and even more preferentially from 10 to 30 minutes.

The cosmetic composition comprising such compounds of leuco type is generally applied to the keratin fibres at room temperature, preferably between 25 and 55° C.

IV. Dyeing Device

The present invention also relates to a multi-compartment device or "kit" comprising a first compartment containing a cosmetic composition comprising one or more compounds of formula (I) as defined previously or containing one or more compounds of leuco type of formula (II) as defined previously, and optionally a second compartment comprising one or more oxidizing agents.

In particular, the invention relates to a multi-compartment dyeing device or "kit" comprising a first compartment containing a cosmetic composition comprising one or more direct dyes of formula (I) as defined previously or containing one or more compounds of leuco type of formula (II) as defined previously, and a second compartment comprising one or more oxidizing agents.

More particularly, the invention relates to a multi-compartment dyeing device or "kit" comprising a first compartment containing a cosmetic composition comprising one or more direct dyes of formula (I) as defined previously, free of oxidizing agent, and a second compartment containing a cosmetic composition comprising one or more oxidizing agents.

The invention also relates to a multi-compartment dyeing device or "kit" comprising a first compartment containing a cosmetic composition comprising one or more compounds of leuco type of the abovementioned formula (II), and a second compartment containing a cosmetic composition comprising one or more oxidizing agents.

According to one particular embodiment, the device may comprise at least one compartment comprising a cosmetic composition comprising one or more compounds of leuco type of the abovementioned formula (II).

In this case, the composition comprising the compound(s) of leuco type as defined above is applied to the keratin fibres, which become coloured due to their exposure to air.

The devices mentioned above are suitable for dyeing keratin fibres.

The evaluation of the coloration can be done visually or read on a spectrocolorimeter (such as Minolta CM3600d, illuminant D65, angle 10°, SCI values) for the $L^*$, $a^*$, $b^*$ colorimetric measurements. In this $L^*$, $a^*$, $b^*$ system, $L^*$ represents the intensity of the color, $a^*$ indicates the green/red color axis and $b^*$ indicates the blue/yellow color axis. The lower the value of L, the darker or more intense the color is. The higher the value of $a^*$, the redder the shade is; the higher the value of $b^*$, the yellower the shade is.

The variation in coloring between the colored locks of natural white hair which is untreated (control) and after treatment or coloration is defined by $\Delta E^*$, corresponding to the color uptake on keratin fibers, according to the following equation:

$$\Delta E^* = \sqrt{(L^* - L_0^*)^2 + (a^* - a_0^*)^2 + (b^* - b_0^*)^2} \qquad (i)$$

In this equation, $L^*$, $a^*$ and $b^*$ represent the values measured after dyeing the natural hair comprising 90% of white hairs and $L_0^*$, $a_0^*$ and $b_0^*$ represent the values measured for the untreated natural hair comprising 90% of white hairs.

The greater the value of $\Delta E$, the greater the difference in color between the control locks and the dyed locks and the greater color uptake is. Chromaticity in the CIE $L^*$, $a^*$, $b^*$ colorimetric system is calculated according to the following equation:

$$C^* = \sqrt{a^{*2} + b^{*2}}$$

The greater the value of $C^*$, the greater the chromaticity is.

The examples that follow serve to illustrate the invention without, however, being limiting in nature.

I—EXAMPLES OF SYNTHESIS

Example 1

Synthesis of 2-(4-amino-2,3-dimethylphenylamino)-5-[(2-hydroxyethyl)methylamino][1,4]benzoquinone (compound 1)

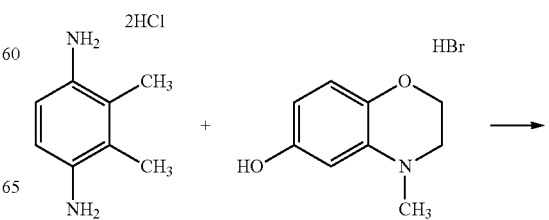

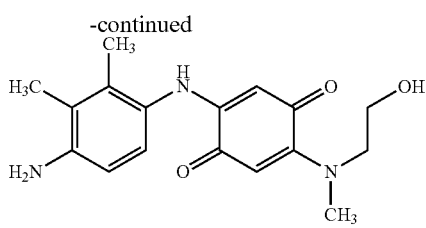

compound 1

To a solution of 1.04 g (0.005 mol) of 2,3-dimethylbenzene-1,4-diamine dihydrochloride in 5 ml of water and 3 ml of 20% aqueous ammonia is added a solution of 1.23 g (0.005 mol) of 4-methyl-3,4-dihydro-2H-1,4-benzoxazin-6-ol hydrobromide in 2 ml of water, 1 ml of 20% aqueous ammonia and 10 ml of acetone. 17 ml of 6% aqueous hydrogen peroxide solution are added and the mixture is stirred at room temperature for 4 hours 30 minutes. After filtering off and drying the precipitate formed, 0.49 g of 2-(4-amino-2,3-dimethylphenylamino)-5-[(2-hydroxyethyl)methylamino]-[1,4]benzoquinone (compound 1) are obtained in the form of a brown powder.

The molecular ion 316 (ES+) is detected by mass spectrometry.

Example 2

Synthesis of 2-[4-(ethylisopropylamino)phenylamino)-5-[(2-hydroxyethyl)methylamino][1,4]benzoquinone (compound 2)

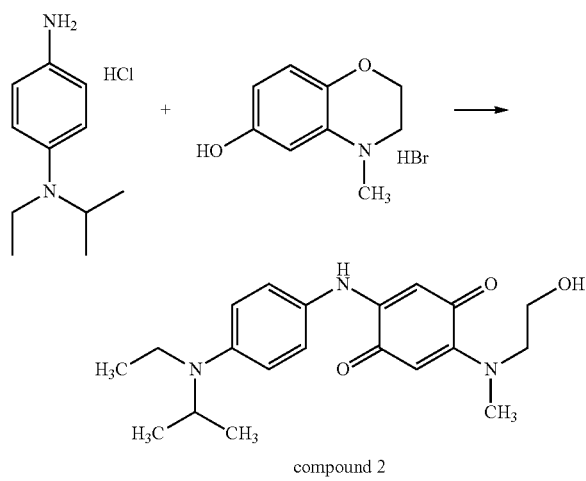

compound 2

To a solution of 1.07 g (0.005 mol) of N-(4-aminophenyl)-N-ethyl-N-isopropylamine hydrochloride in 5 ml of water and 2 ml of 20% aqueous ammonia is added a solution of 1.22 g (0.005 mol) of 4-methyl-3,4-dihydro-2H-1,4-benzoxazin-6-ol hydrobromide in 2 ml of water, 1 ml of 20% aqueous ammonia and 15 ml of acetone. 17 ml of aqueous hydrogen peroxide solution are added and the mixture is stirred at room temperature for 4 hours. An oil forms. After 24 hours at 6° C., the oil forms a gum. This gum is taken up in ethyl acetate. After drying and concentrating this organic phase, 0.86 g of 2-[4-(ethylisopropylamino)phenylamino]-5-[(2-hydroxyethyl)methylamino][1,4]benzoquinone (compound 2) is obtained in the form of a black powder.

The molecular ion 358 (ES+) is detected by mass spectrometry.

Example 3

Synthesis of 2-(4-amino-2,3-dimethylphenylamino)-5-[(2-hydroxyethyl)ethylamino][1,4]benzoquinone (compound 10)

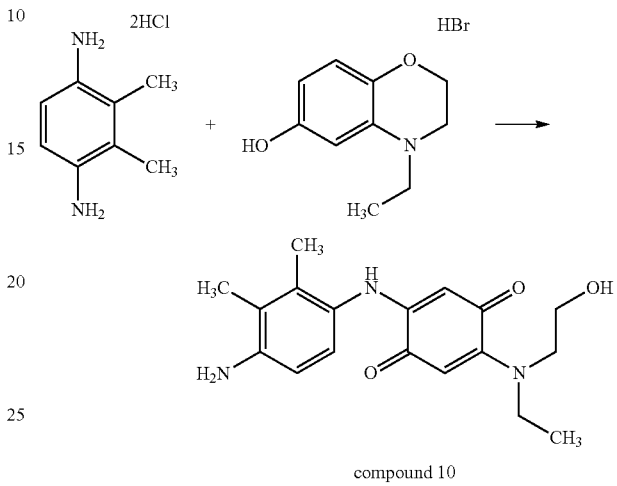

compound 10

To a solution of 1.05 g (0.005 mol) of 2,3-dimethylbenzene-1,4-diamine dihydrochloride in 5 ml of water and 3 ml of 20% aqueous ammonia is added a solution of 1.31 g (0.005 mol) of 4-ethyl-3,4-dihydro-2H-1,4-benzoxazin-6-ol hydrobromide in 3 ml of water, 1 ml of 20% aqueous ammonia and 15 ml of acetone. 17 ml of 6% aqueous hydrogen peroxide solution are added and the mixture is stirred at room temperature for 6 hours 30 minutes. After 12 hours at 6° C., the reaction medium is concentrated and left for a further 12 hours at 6° C. A precipitate forms, which is filtered off. It is purified by chromatography, eluting with dichloromethane/methanol. 0.01 g of 2-(4-amino-2,3-dimethylphenylamino)-5-[(2-hydroxyethyl)ethylamino][1,4]benzoquinone (compound 10) is obtained in the form of a brown powder.

The molecular ion 328 (ES−) is detected by mass spectrometry.

Example 4

Synthesis of 2-[4-(ethylisopropylamino)phenylamino)-5-[(2-hydroxyethyl)ethylamino][1,4]benzoquinone (compound 11)

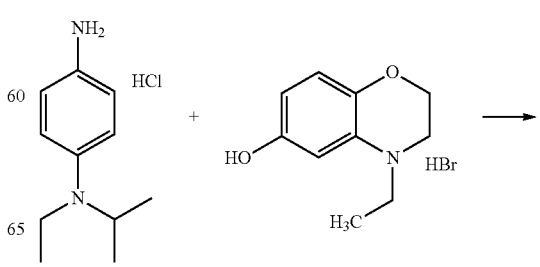

-continued

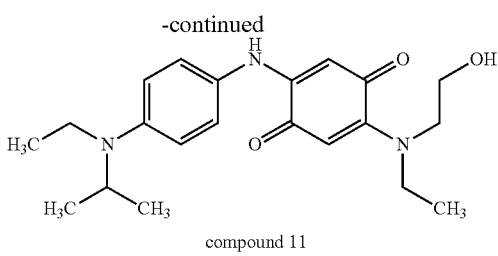

compound 11

To a solution of 1.10 g (0.005 mol) of N-(4-aminophenyl)-N-ethyl-N-isopropylamine hydrochloride in 5 ml of water and 3 ml of 20% aqueous ammonia is added a solution of 1.30 g (0.005 mol) of 4-ethyl-3,4-dihydro-2H-1,4-benzoxazin-6-ol hydrobromide in 3 ml of water, 1 ml of 20% aqueous ammonia and 15 ml of acetone. 17 ml of aqueous hydrogen peroxide solution are added and the mixture is stirred at room temperature for 3 hours 30 minutes. An oil forms. After 12 hours at 6° C., the oil forms a gum. This gum is taken up in ethyl acetate, dried over disodium sulfate and filtered, and the ethyl acetate is evaporated off. The product is purified on a column of silica (eluent: 80/20 ethyl acetate/heptane). The eluent is evaporated off. After 48 hours at 6° C., the product has crystallized, and is left to dry. 0.52 g of 2-[4-(ethylisopropylamino)phenylamino)-5-[(2-hydroxyethyl)ethylamino][1,4]benzoquinone (compound 11) is obtained.

The molecular ion 372 (ES+) is detected by mass spectrometry.

Example 5

Synthesis of 2-(3-chloro-4-hydroxyphenylamino)-5-[(2-hydroxyethyl)methylamino][1,4]benzoquinone (compound 7)

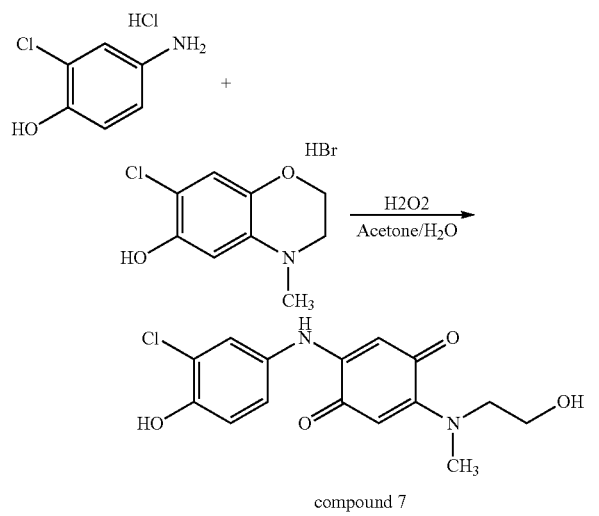

compound 7

To a solution of 0.90 g (0.005 mol) of 4-amino-2-chlorophenol hydrochloride in 5 ml of water and 2 ml of 20% aqueous ammonia is added a solution of 1.23 g (0.005 mol) of 4-methyl-3,4-dihydro-2H-1,4-benzoxazin-6-ol hydrobromide in 3 ml of water, 1 ml of 20% aqueous ammonia and 10 ml of acetone. The pH is adjusted to 9.5 with 20% aqueous ammonia. 17 ml of 6% aqueous hydrogen peroxide solution are added. After 3 hours, the precipitate is filtered off. 0.99 g of 2-(3-chloro-4-hydroxyphenylamino)-5-[(2-hydroxyethyl)methylamino][1,4]benzoquinone (compound 7) is obtained in the form of a brown powder.

The molecular ion 323 (ES+) is detected by mass spectrometry.

Example 6

Synthesis of 2-(2-chloro-4-hydroxyphenylamino)-5-[(2-hydroxyethyl)methylamino][1,4]benzoquinone (compound 4)

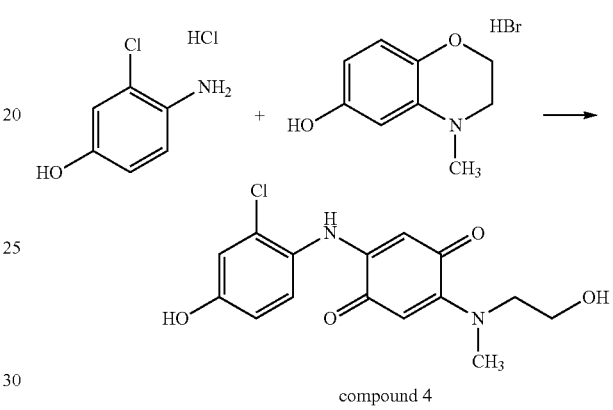

compound 4

To a solution of 0.90 g (0.005 mol) of 4-amino-3-chlorophenol hydrochloride in 8 ml of water and 2 ml of 20% aqueous ammonia is added a solution of 1.23 g (0.005 mol) of 4-methyl-3,4-dihydro-2H-1,4-benzoxazin-6-ol hydrobromide in 3 ml of water, 1 ml of 20% aqueous ammonia and 10 ml of acetone. 17 ml of 6% aqueous hydrogen peroxide solution are added and the mixture is stirred at room temperature for 6 hours 30 minutes. After 12 hours at 6° C., the precipitate formed is filtered off and dried. The product is purified on a column of silica (eluent: 100% dichloromethane and then dichloromethane/methanol up to 10% methanol). 0.01 g of 2-(2-chloro-4-hydroxyphenylamino)-5-[(2-hydroxyethyl)methylamino][1,4]benzoquinone (compound 4) is obtained.

The molecular ion 323 (ES+) is detected by mass spectrometry.

Example 7

Synthesis of 2-[(4-amino-2,3-dimethylphenyl)amino]-5-[(2 hydroxyethyl)(methyl)amino]benzene-1,4-diol (compound 32)

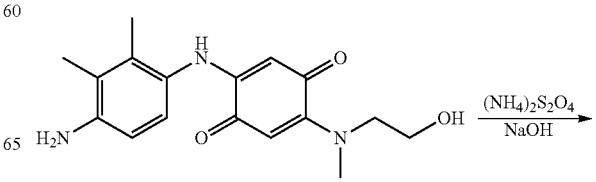

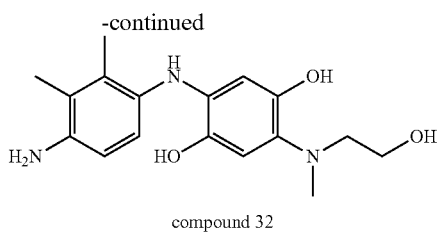

compound 32

To a solution of 5 mg of 2-(4-amino-2,3-dimethylphenylamino)-5-[(2-hydroxyethyl)methylamino][1,4]benzoquinone 1 in 2 ml of 0.5M sodium hydroxide are added 15 mg of dithionite in 2 ml of water, and the mixture is stirred until decolorized.

The molecular ion 318 (ES+) is detected by mass spectrometry.

II—DYEING EVALUATION OF THE COMPOUNDS

The following dye compositions were prepared:
500 mg of illustrated compound
79 g of water,
15 g of ethanol,
5 g of benzyl alcohol,
0.5 g of benzoic acid.

1 g of the mixture is applied to a lock of 0.25 g of grey hair containing 90% white hairs. After a leave-on time of 30 minutes, the lock is rinsed, washed with a standard shampoo, rinsed again and then dried.

The results are collated in the following table:

| Compound 1 | Yellowish brown |
| Compound 2 | Greenish brown |
| Compound 10 | Yellowish brown |
| Compound 11 | Dark greenish brown |
| Compound 7 | Golden |
| Compound 4 | Golden |

III. COMPARATIVE EXAMPLES

The following dyes were compared:

Compound 3

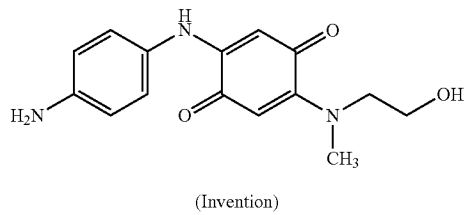

(Invention)

Compound A

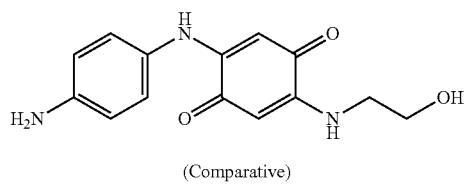

(Comparative)

The dye compositions were prepared as follows:

5 mg of dye (compound 3 or compound A) were added to 1 g of dye support constituted of 0.5% by weight of benzoic acid, 5% by weight of benzyl alcohol, 15% by weight of ethanol and 79.5% by weight of water relative to the total weight of the dye composition.

The pH of the compositions was adjusted to 9.5 with aqueous ammonia containing 20% of $NH_3$.

The mixture is applied to a lock of 0.25 g of grey hair containing 90% white hairs. After a leave-on time of 30 minutes at ambient temperature, the lock is washed with a standard shampoo.

The evaluation of the coloration is done with a spectrocolorimeter (such as Minolta CM3600d, illuminant D65, angle 10°, SCI values) for the $L^*$, $a^*$, $b^*$ colorimetric measurements.

The variation in coloring between the colored locks of natural white hair which is untreated (control) and after treatment or coloration defined by $\Delta E^*$ is calculated according to equation (i) as previously mentioned.

Results

|  | $L^*$(D65) | $a^*$(D65) | $b^*$(D65) | $\Delta E^*$ (D65) |
|---|---|---|---|---|
| Composition 1 (compound 3) | 46.8 | −0.8 | 24.3 | 20.1 |
| Composition 1 (Compound A) | 61.6 | 0.1 | 15.2 | 2.8 |

According to these results, the dye of the present invention (compound 3) leads to a more intense and chromatic coloration than the comparative dye (compound A) in the same dyeing composition.

Furthermore, the colour uptake is significantly higher with compound 3 than with compound A.

The invention claimed is:

1. A quinone direct dye of formula (I), the organic or mineral acid or base salts thereof, the tautomeric forms thereof, the optical isomers or geometrical isomers thereof, and/or the solvates thereof:

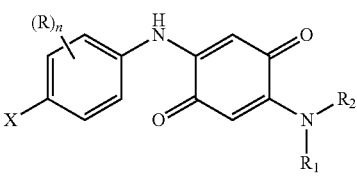

(I)

wherein:
n is an integer equal to 0, 1, 2, 3 or 4;
R is chosen from:
  a linear or branched $C_1$-$C_4$ alkyl radical,
  a linear or branched $C_1$-$C_4$ alkyl radical substituted with at least one radical chosen from hydroxyl, imidazolium, and An radicals, wherein An represents a cosmetically acceptable anion or combination of anions,
  a $C_1$-$C_4$ alkoxy radical, and
  a halogen atom;
$R_1$ is chosen from:
  a linear or branched $C_1$-$C_5$ alkyl radical, and
  a linear or branched $C_1$-$C_5$ alkyl radical substituted with at least one hydroxyl radical;

R₂ is chosen from:
- a linear or branched $C_1$-$C_5$ alkyl radical, and
- a linear or branched $C_1$-$C_5$ alkyl radical substituted with at least one hydroxyl radical;

X is chosen from:
- a hydroxyl radical, and
- a radical —NR₃R₄ wherein R₃ and R₄ represent, independently of each other:
  - a hydrogen atom;
  - a linear or branched $C_1$-$C_6$ alkyl radical;
  - a linear or branched $C_1$-$C_6$ alkyl radical, substituted with at least one hydroxyl or $C_1$-$C_4$ alkoxy radical.

2. The quinone direct dye of formula (I) according to claim 1, wherein:
n is an integer equal to 0, 1 or 2;
R is chosen from:
- a linear or branched $C_1$-$C_4$ alkyl radical,
- a $C_1$-$C_4$ alkoxy radical, and
- a halogen atom;

$R_1$ is chosen from:
- a linear or branched $C_1$-$C_5$ alkyl radical,
- a linear or branched $C_1$-$C_5$ alkyl radical substituted with at least one hydroxyl radical;

$R_2$ is chosen from:
- a linear or branched $C_1$-$C_5$ alkyl radical,
- a linear or branched $C_1$-$C_5$ alkyl radical substituted with at least one hydroxyl radical; and X is chosen from:
- a hydroxyl radical;
- a radical —NR₃R₄ wherein R₃ and R₄, which may be identical or different, are chosen from:
  - a hydrogen atom,
  - a linear or branched $C_1$-$C_6$ alkyl radical, and
  - a linear or branched $C_1$-$C_6$ alkyl radical substituted with at least one hydroxyl radical.

3. The quinone direct dye of formula (I) according to claim 1, wherein n is an integer equal to 0, 1 or 2.

4. The quinone direct dye of formula (I) according to claim 1, wherein $R_1$ is a linear or branched $C_1$-$C_5$ alkyl radical and $R_2$ is a linear or branched $C_1$-$C_5$ alkyl radical substituted with at least one hydroxyl radical, or wherein $R_2$ is a linear or branched $C_1$-$C_5$ alkyl radical and $R_1$ is a linear or branched $C_1$-$C_5$ alkyl radical substituted with at least one hydroxyl radical.

5. The quinone direct dye of formula (I) according to claim 1, wherein $R_1$ is chosen from a methyl radical and an ethyl radical, and $R_2$ is a 2-hydroxyethyl radical, or wherein $R_2$ is chosen from a methyl radical and an ethyl radical, and $R_1$ is a 2-hydroxyethyl radical.

6. The quinone direct dye of formula (I) according to claim 1, wherein the compound is chosen from the following compounds and the geometrical or optical isomer forms thereof, the tautomers thereof, the organic or mineral acid or base salts thereof, and the solvates thereof:

Compound 1

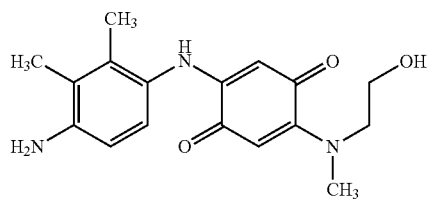

2-(4-Amino-2,3-dimethylphenylamino-5-[2-hydroxyethyl)methylamino][1,4]benzoquinone Compound 2

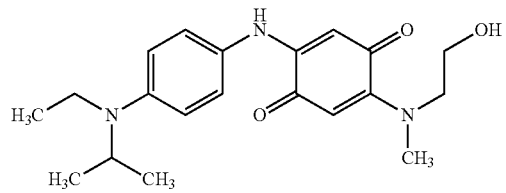

2-[4-(Ethylisopropylamino)phenylamino]-5-[(2-hydroxyethyl)methylamino][1,4]benzoquinone Compound 3

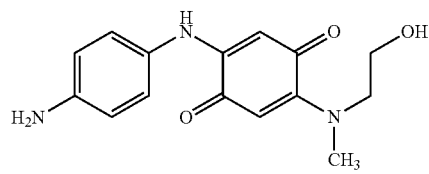

2-(4-Aminophenylamino)-5-[(2-hydroxyethyl)methylamino][1,4]benzoquinone

Compound 4

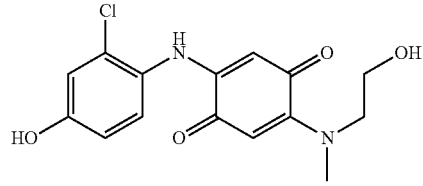

2-(2-Chloro-4-hydroxyphenylamino)-5-[(2-hydroxyethyl)methylamino][1,4]benzoquinone Compound 5

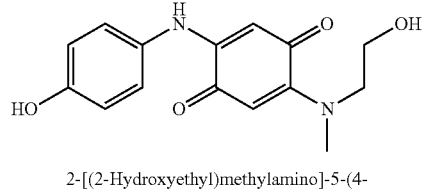

2-[(2-Hydroxyethyl)methylamino]-5-(4-hydroxyphenylamino)[1,4]benzoquinone

Compound 6

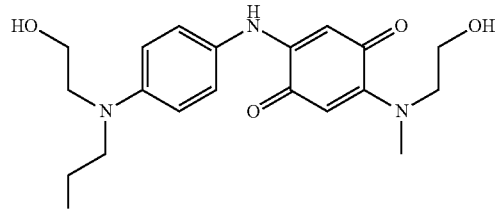

2-{4-[Bis(2-hydroxyethyl)amino]phenylamino}-5-[(2-hydroxyethyl)methylamino][1,4]benzoquinone Compound 7

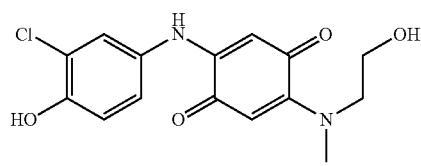

2-(3-Chloro-4-hydroxyphenylamino)-5-[(2-hydroxyethyl)methylamino][1,4]benzoquinone Compound 8

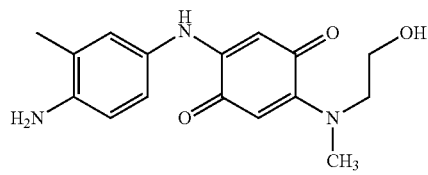

2-(4-Amino-3-methylphenylamino)-5-[(2-hydroxyethyl)methylamino][1,4]benzoquinone Compound 9

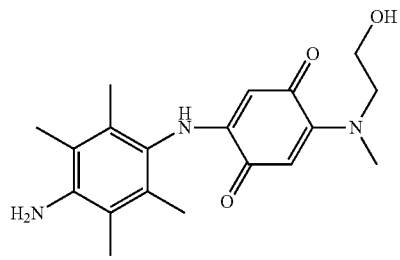

2-(4-Amino-2,3,5,6-tetramethylphenylamino)-5-[(2-hydroxyethyl)methylamino][1,4]benzoquinone Compound 10

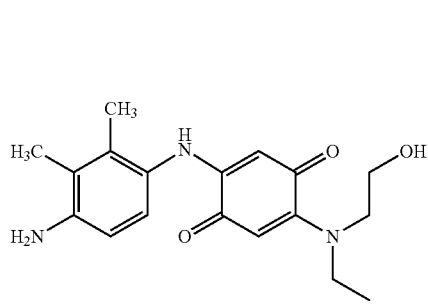

2-(4-Amino-2,3-dimethylphenylamino)-5-[(2-hydroxyethyl)ethylamino][1,4]benzoquinone Compound 11

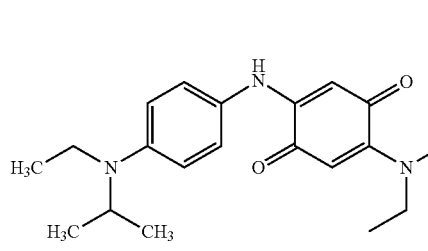

2-[4-(Ethylisopropylamino)phenylamino]-5-[(2-hydroxyethyl)ethylamino][1,4]benzoquinone Compound 12

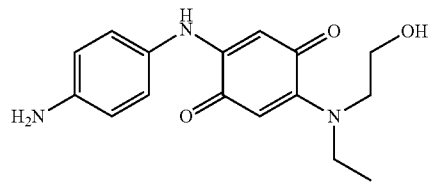

2-(4-(Aminophenylamino)-5-[(2-hydroxyethyl)ethylamino][1,4]benzoquinone

Compound 13

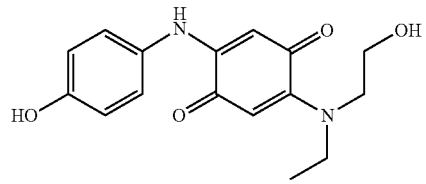

2-[(2-Hydroxyethyl)ethylamino]-5-(4-hydroxyphenylamino)[1,4]benzoquinone

Compound 14

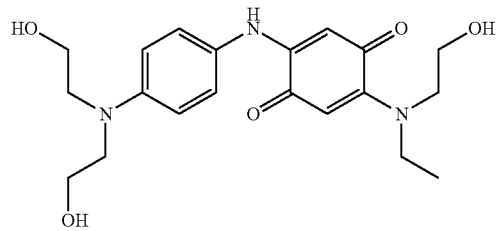

2-{4-[Bis(2-hydroxyethyl)amino]phenylamino}-5-[(2-hydroxyethyl)ethylamino][1,4]benzoquinone Compound 15

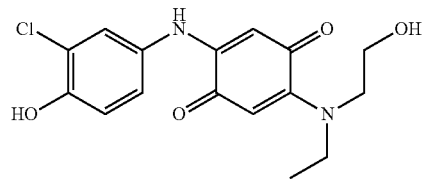

2-(3-Chloro-4-hydroxyphenylamino)-5-[(2-hydroxyethyl)ethylamino][1,4]benzoquinone Compound 16

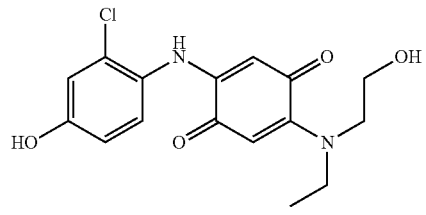

2-(2-Chloro-4-hydroxyphenylamino)-5-[ethyl-(2-hydroxyethyl)amino][1,4]benzoquinone Compound 17

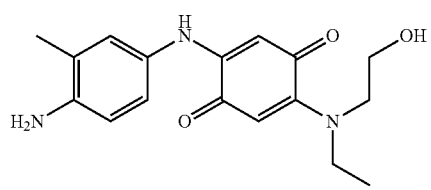

2-(4-Amino-3-methylphenylamino)-5-[(2-hydroxyethyl)ethylamino][1,4]benzoquinone

Compound 18

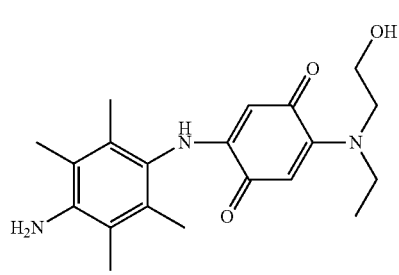

2-(4-Amino-2,3,5,6-tetramethylphenylamino)-5-[(2-hydroxyethyl)ethylamino][1,4]benzoquinone Compound 19

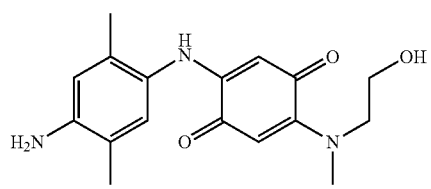

2-(4-Amino-2,5-dimethylphenylamino)-5-[(2-hydroxyethyl)methylamino][1,4]benzoquinone Compound 20

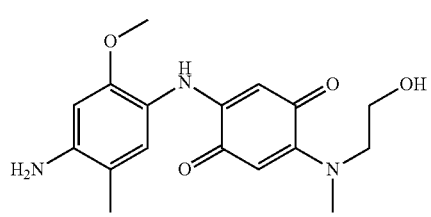

2-(4-Amino-2-methoxy-5-methylphenylamino)-5-[(2-hydroxyethyl)methylamino][1,4]benzoquinone Compound 21

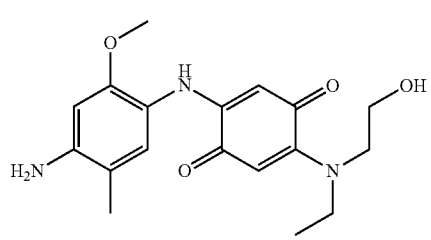

2-(4-Amino-2-methoxy-5-methylphenylamino)-5-[ethyl-(2-hydroxyethyl)amino][1,4]benzoquinone Compound 22

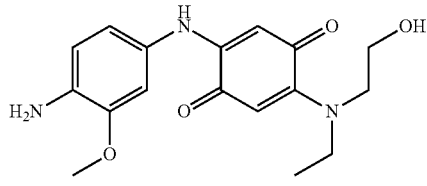

2-(4-Amino-3-methoxyphenylamino)-5-[ethyl-(2-hydroxyethyl)amino][1,4]benzoquinone Compound 23

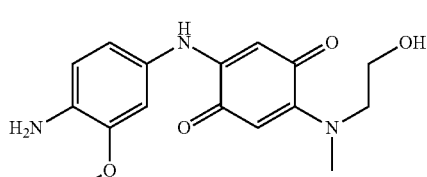

2-(4-Amino-3-methoxyphenylamino)-5-[(2-hydroxyethyl)methylamino][1,4]benzoquinone Compound 24

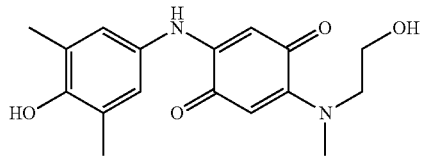

2-(4-Hydroxy-3,5-dimethylphenylamino)-5-[(2-hydroxyethyl)methylamino][1,4]benzoquinone Compound 25

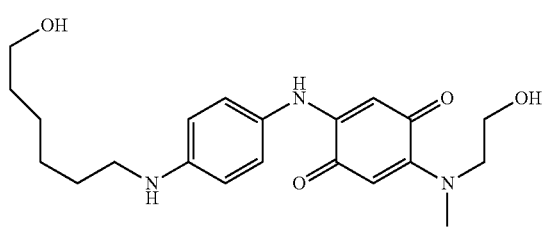

2-(4-Hydroxy-2,5-dimethylphenylamino)-5-[(2-hydroxyethyl)methylamino][1,4]benzoquinone Compound 26

2-[(2-Hydroxyethyl)methylamino]-5-[4-(6-hydroxy-hexylamino)phenylamino][1,4]benzoquinone Compound 27

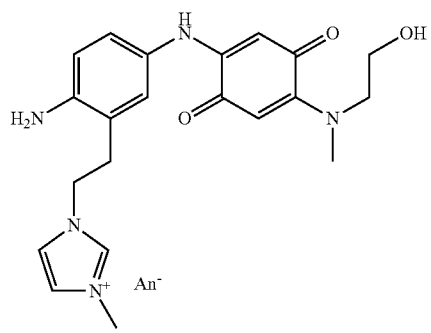

3-[2-(2-Amino-5-{4-[(2-hydroxyethyl)methylamino]-3,6-dioxocyclohexa-1,4-dienylamino}phenyl)ethyl]-1-methyl-3H-imidazol-1-ium salt Compound 28

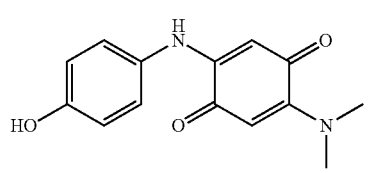

2-Dimethylamino-5-(4-hydroxyphenylamino)[1,4]benzoquinone

Compound 29

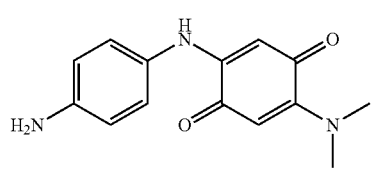

2-(4-Aminophenylamino)-5-dimethylamino)[1,4]benzoquinone

Compound 30

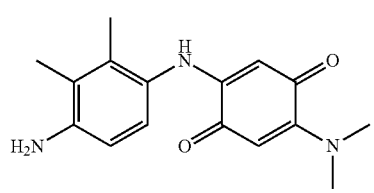

2-(4-Amino-2,3-dimethylphenylamino)-5-dimethylamino)[1,4]benzoquinone

Compound 31

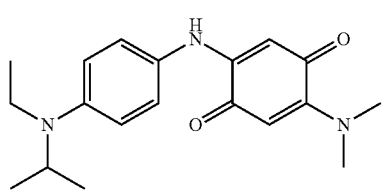

2-Dimethylamino-5-[4-(ethylisopropylamino)phenyl-amino][1,4]benzoquinone

Compound 32

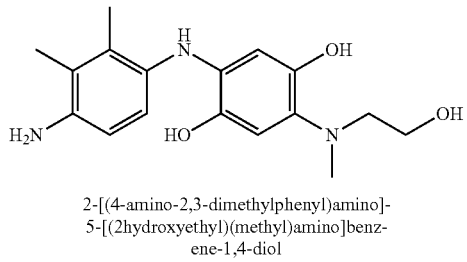

2-[(4-amino-2,3-dimethylphenyl)amino]-5-[(2hydroxyethyl)(methyl)amino]benzene-1,4-diol Compound 33

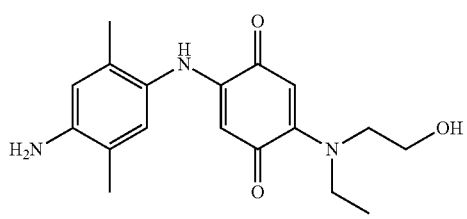

2-(4-amino-2,5-dimethylphenylamino)-5-[(2-hydroxyethyl)methylamino][1,4]benzene-1,4-diol with An⁻ denoting a cosmetically acceptable anion or a mixture of cosmetically acceptable anions.

7. A composition for dyeing keratin fibers, comprising, in a suitable dyeing medium, at least one quinone direct dye of formula (I):

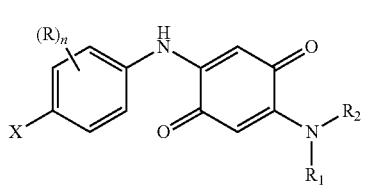

wherein:
n is an integer equal to 0, 1, 2, 3 or 4;
R is chosen from:
  a linear or branched $C_1$-$C_4$ alkyl radical,
  a linear or branched $C_1$-$C_4$ alkyl radical substituted with at least one radical chosen from hydroxyl, imidazolium, and An radicals, wherein An represents a cosmetically acceptable anion or combination of anions,
  a $C_1$-$C_4$ alkoxy radical, and
  a halogen atom;
$R_1$ is chosen from:
  a linear or branched $C_1$-$C_5$ alkyl radical, and
  a linear or branched $C_1$-$C_5$ alkyl radical substituted with at least one hydroxyl radicals;
$R_2$ is chosen from:
  a linear or branched $C_1$-$C_5$ alkyl radical, and
  a linear or branched $C_1$-$C_5$ alkyl radical substituted with at least one hydroxyl radical;
X is chosen from:
  a hydroxyl radical, and
  a radical —$NR_3R_4$ wherein $R_3$ and $R_4$ represent, independently of each other:
    a hydrogen atom;
    a linear or branched $C_1$-$C_6$ alkyl radical;
    a linear or branched $C_1$-$C_6$ alkyl radical, substituted with at least one hydroxyl or $C_1$-$C_4$ alkoxy radical.

8. A method for dyeing keratin fibers, the method comprising:
applying to the keratin fibers a dye composition comprising, in a suitable dyeing medium, for a time sufficient to obtain a desired coloration, at least one quinone direct dye of formula (I):

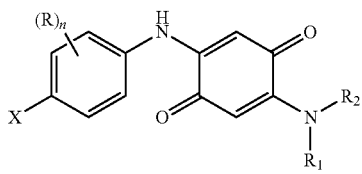

(I)

wherein:
n is an integer equal to 0, 1, 2, 3 or 4;
R is chosen from:
a linear or branched $C_1$-$C_4$ alkyl radical,
a linear or branched $C_1$-$C_4$ alkyl radical substituted with at least one radical chosen from hydroxyl, imidazolium, and An radicals, wherein An represents a cosmetically acceptable anion or combination of anions,
a $C_1$-$C_4$ alkoxy radical, and
a halogen atom;
$R_1$ is chosen from:
a linear or branched $C_1$-$C_5$ alkyl radical, and
a linear or branched $C_1$-$C_5$ alkyl radical substituted with at least one hydroxyl radicals;
$R_2$ is chosen from:
a linear or branched $C_1$-$C_5$ alkyl radical, and
a linear or branched $C_1$-$C_5$ alkyl radical substituted with at least one hydroxyl radical;
X is chosen from:
a hydroxyl radical, and
a radical —$NR_3R_4$ wherein $R_3$ and $R_4$ represent, independently of each other:
a hydrogen atom;
a linear or branched $C_1$-$C_6$ alkyl radical;
a linear or branched $C_1$-$C_6$ alkyl radical, substituted with at least one hydroxyl or $C_1$-$C_4$ alkoxy radical;
rinsing the fibers;
optionally washing the fibers with shampoo;
optionally rinsing the fibers; and
drying the keratin fibers or leaving the keratin fibers to dry.

9. A method for lightening keratin fibers, the method comprising:
applying a dye composition comprising, in a suitable dyeing medium, (i) at least one quinone direct dye of formula (I) free of oxidizing agent, and (ii) a cosmetic composition comprising at least one oxidizing agent, wherein compositions (i) and (ii) are applied to the keratin fibers sequentially or simultaneously for a time that is sufficient to obtain a desired lightening:

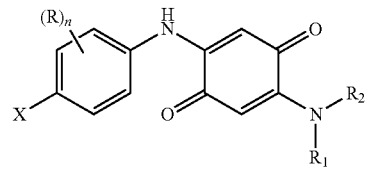

(I)

wherein:
n is an integer equal to 0, 1, 2, 3 or 4;
R is chosen from:
a linear or branched $C_1$-$C_4$ alkyl radical,
a linear or branched $C_1$-$C_4$ alkyl radical substituted with at least one radical chosen from hydroxyl, imidazolium, and An radicals, wherein An represents a cosmetically acceptable anion or combination of anions,
a $C_1$-$C_4$ alkoxy radical, and
a halogen atom;
$R_1$ is chosen from:
a linear or branched $C_1$-$C_5$ alkyl radical, and
a linear or branched $C_1$-$C_5$ alkyl radical substituted with at least one hydroxyl radicals;
$R_2$ is chosen from:
a linear or branched $C_1$-$C_5$ alkyl radical, and
a linear or branched $C_1$-$C_5$ alkyl radical substituted with at least one hydroxyl radical;
X is chosen from:
a hydroxyl radical, and
a radical —$NR_3R_4$ wherein $R_3$ and $R_4$ represent, independently of each other:
a hydrogen atom;
a linear or branched $C_1$-$C_6$ alkyl radical;
a linear or branched $C_1$-$C_6$ alkyl radical, substituted with at least one hydroxyl or $C_1$-$C_4$ alkoxy radical;
rinsing the fibers;
optionally washing the fibers with shampoo;
optionally rinsing the fibers; and
drying the fibers or leaving the fibers to dry.

10. A leuco type compound of formula (II), the organic or mineral acid or base salts thereof, the tautomeric forms thereof, the optical isomers or geometrical isomers thereof, and the solvates thereof:

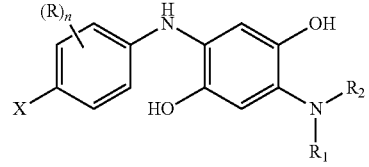

(II)

wherein:
n is an integer equal to 0, 1, 2, 3 or 4;
R is chosen from:
a linear or branched $C_1$-$C_4$ alkyl radical,
a linear or branched $C_1$-$C_4$ alkyl radical substituted with at least one radical chosen from hydroxyl, imidazolium, and An radicals, wherein An represents a cosmetically acceptable anion or combination of anions,
a $C_1$-$C_4$ alkoxy radical, and
a halogen atom;

$R_1$ is chosen from:
- a linear or branched $C_1$-$C_5$ alkyl radical, and
- a linear or branched $C_1$-$C_5$ alkyl radical substituted with at least one hydroxyl radicals;

$R_2$ is chosen from:
- a linear or branched $C_1$-$C_5$ alkyl radical, and
- a linear or branched $C_1$-$C_5$ alkyl radical substituted with at least one hydroxyl radical;

X is chosen from:
- a hydroxyl radical, and
- a radical —$NR_3R_4$ wherein $R_3$ and $R_4$ represent, independently of each other:
  - a hydrogen atom;
  - a linear or branched $C_1$-$C_6$ alkyl radical;
- a linear or branched $C_1$-$C_6$ alkyl radical, substituted with at least one hydroxyl or $C_1$-$C_4$ alkoxy radical.

11. A composition for dyeing keratin fibers, comprising at least one leuco-type compound of formula (II) as defined according to claim 10.

12. A method for dyeing keratin fibers, the method comprising:
applying to the keratin fibers, which may be wet or dry, simultaneously or sequentially (i) a dye composition comprising at least one compound of formula (II), and (ii) an oxidizing composition comprising at least one oxidizing agent:

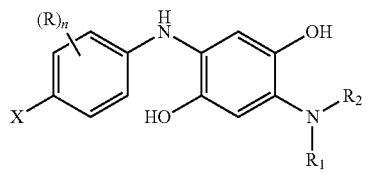

(II)

wherein:
n is an integer equal to 0, 1, 2, 3 or 4;
R is chosen from:
- a linear or branched $C_1$-$C_4$ alkyl radical,
- a linear or branched $C_1$-$C_4$ alkyl radical substituted with at least one radical chosen from hydroxyl, imidazolium, and An radicals, wherein An represents a cosmetically acceptable anion or combination of anions,
- a $C_1$-$C_4$ alkoxy radical, and
- a halogen atom;

$R_1$ is chosen from:
- a linear or branched $C_1$-$C_5$ alkyl radical, and
- a linear or branched $C_1$-$C_5$ alkyl radical substituted with at least one hydroxyl radicals;

$R_2$ is chosen from:
- a linear or branched $C_1$-$C_5$ alkyl radical, and
- a linear or branched $C_1$-$C_5$ alkyl radical substituted with at least one hydroxyl radical;

X is chosen from:
- a hydroxyl radical, and
- a radical —$NR_3R_4$ wherein $R_3$ and $R_4$ represent, independently of each other:
  - a hydrogen atom;
  - a linear or branched $C_1$-$C_6$ alkyl radical;
- a linear or branched $C_1$-$C_6$ alkyl radical, substituted with at least one hydroxyl or $C_1$-$C_4$ alkoxy radical.

13. A multi-compartment kit comprising a first compartment configured to contain the dye composition according to claim 7, and a second compartment comprising at least one oxidizing agent.

14. A multi-compartment kit comprising a first compartment configured to contain the dye composition according to claim 7, and a second compartment comprising a cosmetic composition comprising at least one oxidizing agent, wherein the first compartment is free of oxidizing agent.

15. A multi-compartment kit comprising a first compartment configured to contain the dye composition according to claim 11, and a second compartment comprising at least one oxidizing agent.

16. A multi-compartment kit comprising a first compartment configured to contain the dye composition according to claim 11, and a second compartment comprising a cosmetic composition comprising at least one oxidizing agent.

* * * * *

UNITED STATES PATENT AND TRADEMARK OFFICE
CERTIFICATE OF CORRECTION

PATENT NO. : 9,233,057 B2  Page 1 of 1
APPLICATION NO. : 14/365224
DATED : January 12, 2016
INVENTOR(S) : Stephane Sabelle It is certified that error appears in the above-identified patent and that said Letters Patent is hereby corrected as shown below:

Claims

Col. 28, line 60, claim 1, change "An" (both occurrences) to -- An- --.

Col. 36, line 49, claim 7, change "An" (both occurrences) to -- An- --.

Col. 37, line 27, claim 8, change "An" (both occurrences) to -- An- --.

Col. 38, line 17, claim 9, change "An" (both occurrences) to -- An- --.

Col. 38, line 64, claim 10, change "An" (both occurrences) to -- An- --.

Col. 40, line 1, claim 12, change "An" to -- An- --.

Signed and Sealed this
Twelfth Day of April, 2016

Michelle K. Lee
*Director of the United States Patent and Trademark Office*